United States Patent
Mons

(10) Patent No.: US 7,448,280 B2
(45) Date of Patent: Nov. 11, 2008

(54) METHOD FOR EVALUATING THE FATIGUE STRENGTH OF WELDED JOINTS

(75) Inventor: Claude Marcel Mons, Savigny le Temple (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 11/833,628

(22) Filed: Aug. 3, 2007

(65) Prior Publication Data

US 2008/0028866 A1    Feb. 7, 2008

(30) Foreign Application Priority Data

Aug. 3, 2006    (FR)    ................... 06 53274

(51) Int. Cl.
*G01N 3/20*    (2006.01)
(52) U.S. Cl. .......................................... 73/850; 73/856
(58) Field of Classification Search .............. 73/850, 73/856, 841, 842, 843, 844
See application file for complete search history.

(56) References Cited

U.S. PATENT DOCUMENTS

| | | | |
|---|---|---|---|
| 4,152,148 A * | 5/1979 | Machmeier | ................. 420/95 |
| 4,343,424 A | 8/1982 | Montemarano et al. | |
| 4,402,227 A | 9/1983 | Hayashi et al. | |
| 5,176,028 A * | 1/1993 | Humphrey | ................. 73/150 A |
| 5,415,047 A * | 5/1995 | Maciejewski et al. | ......... 73/850 |
| 6,193,133 B1 * | 2/2001 | Kagan et al. | ................. 228/103 |
| 2004/0112141 A1 | 6/2004 | Murakami | |
| 2006/0236765 A1 | 10/2006 | Bouet et al. | |

FOREIGN PATENT DOCUMENTS

SU        1509208 A1    9/1989

OTHER PUBLICATIONS

W.R. Oates, et al., "Welding Metallurgy of Titanium and Titanium Alloys," Titanium and Titanium Alloys, Welding Handbook - vol. 4 - Materials and applications, part 2, 1998, American Welding Society, XP002425725, pp. 500-506 and 514-519.

* cited by examiner

*Primary Examiner*—Jewel V Thompson
(74) *Attorney, Agent, or Firm*—Oblon, Spivak, McClelland, Maier & Neustadt, P.C.

(57) ABSTRACT

Method for evaluating the fatigue strength of welded joints produced by melting an alloy using a specified welding technique, which method comprises the following steps:
- a statistically significant number N of specimens are produced with a welded joint using said welding technique;
- each of the specimens is subjected to cyclic fatigue tests, with an alternating stress a, until failure;
- the size of the relevant defect appearing in the fracture plane of the specimens is measured by fractography;
- a range of defect dimensions for which the probability of measuring by fractography a defect outside the range is less than a predetermined level of probability t is determined from the measured sizes; and
- the lowest stress $\sigma_{min}$ liable to cause the specimen to fail with a level of probability t is determined from this range.

5 Claims, 2 Drawing Sheets

METHOD FOR EVALUATING THE FATIGUE STRENGTH OF WELDED JOINTS

BACKGROUND OF THE INVENTION

The present invention relates to the field of welding.

DESCRIPTION OF THE PRIOR ART

There are various methods for joining two metal parts together. In particular, the parts may be joined by supplying heat, causing the metal to melt or diffuse. TIG, plasma, laser or inertia friction welding techniques are for example known. Moreover, missing metal on a part, for example resulting from wear, may be repaired by material resurfacing by means of a molten metal. In this case too, TIG, plasma, microplasma or other welding techniques are employed.

When considering the field of turbomachines, the metal parts thus resurfaced or joined may often be subjected to cyclically repeated vibrations, stresses or strains. This fatigue stressing may result prematurely in destruction of the welded joints.

In the majority of cases, postmortem fractographic analyses show that the parts originally had defects that initiated fatigue cracks. These are small defects, of the blowhole or inclusion type, generally too small to be detectable by standard non-destructive testing means, often denoted by the term NDT. Depending on the alloy and the assembly geometry, these NDT means use techniques involving in particular radiography, ultrasound or video tape recording.

It is known by those skilled in the art that relevant fatigue defects, that is to say defects that are the origin of joint failures, have sizes of around 5 to 10 times smaller than those of defects that can be detected with sufficient probability by NDT means. Thus, such defects may have a size of 40 to 70 μm, whereas defects detectable by NDT means have a size of about 150 to 300 μm.

This difference precludes the creation of an objective link between defects relevant in fatigue, and therefore the lifetime of the weld, and the defects that are detected.

This point puts fusion-welded joints at a disadvantage, by the imposition of safety factors, and it makes it impossible, by using nondestructive testing means, to make an objective distinction between two types of welding method through their defects. Any weld having defects below the threshold for detection by the NDT means will be judged to be identical, whether the defects generated are close to the threshold or are much smaller. The link with fatigue strength is therefore not objective.

The objective of the invention is to develop a method that makes it possible to guarantee the minimum fatigue levels for defects that are not detectable by nondestructive testing (NDT) means.

This objective is achieved by the invention by using the approach consisting in determining the influence of welding defects on the fatigue strength of welded joints using one of the abovementioned welding methods.

SUMMARY OF THE INVENTION

Thus, according to the invention, the method for evaluating the fatigue strength of welded joints produced by melting an alloy using a specified welding technique comprises the following steps:

a statistically significant number N of specimens are produced with a welded joint using said welding technique;

the specimens are subjected to cyclic fatigue tests, with an alternating stress σ, until they fail;

the size of the relevant defect appearing in the fracture plane of the specimens is measured by fractography;

a range of defect dimensions for which the probability of measuring by fractography a defect outside the range is less than a predetermined level of probability t is determined from the measured sizes; and the lowest stress $\sigma_{min}$ liable to cause the specimen to fail with a level of probability t is determined from this range.

Preferably, the method relates to a welding technique which employs a laser beam to melt the alloy.

The term "welded joint" covers both assemblies of parts welded together and resurfacing by addition of material. A welded joint forms the junction between parts in an assembly, but the invention also relates to the resurfacing, by addition of molten metal, of missing portions in a part. For example, the invention applies within the context of repairing titanium alloy turbomachine blades. In this case, a known welding technique is used to reconstruct the tip of blades by depositing molten metal in a laser beam. According to another known technique, a part is welded onto the missing portion of a blade under repair.

Knowing the minimum stress value, it is possible to determine the lowering in strength of the welded joint compared with the sound material, that is to say the material away from the heat-affected zone, which material has not undergone melting or alteration during welding of the bead.

According to another feature, a welded joint is produced on the specimens, the volume of which is between 10 and 100% of the welded joint on the parts to be assembled.

The invention applies in particular to the evaluation in fatigue of titanium alloy welded joints; the statistically significant number of specimens is then between 35 and 40, preferably 40.

According to another feature, the level of probability t is less than 1%, this corresponding to the normality range extending between sizes corresponding to the mean less three standard deviations and the mean plus three standard deviations. More particularly, the confidence level is 99.7%.

Thus, the method as claimed has the advantage of gaining access to the actual impact, in the fatigue of welded assemblies, of the relevant defects, whereas these cannot be measured in standard NDT.

The method gives the manufacturer of welded parts the capability of:

displaying size minima; and discriminating between assembly or resurfacing methods producing defects of variable size, but lying below the NDT detection thresholds and thus making an objective process choice possible.

A statistically sufficient number of specimens with two major items of information are produced, namely the lifetime and the size of the original defects. These two distributions of results show that defects relevant in the case of application of the method, namely electron beam welding on TA6V titanium alloy sheets or laser resurfacing on Ti17 blades, have sizes very far below the detection threshold, namely 40 to 70 μm as opposed to 300 μm, that they are reproducible and that their distribution controls the lifetime. The statistical distribution of defects and the distribution of lifetime are of the same nature. It is therefore possible, for a set of welding or resurfacing parameters, to define a minimum lifetime of the assembly for a given reliability. Comparison of the results with the minimum determined by the base trials therefore gives a reliable value of the lowering in fatigue behavior owing to the process employed with the industrial parameters, and a link with the distribution of defects.

In practice, quantifying welding or resurfacing sources using different parameters involves fatigue testing and fractographic examination of relevant defect distributions. It is considered that the design downgrading is the same in both cases.

The method described in patent U.S. 2004/112141 relates only to steels, covers the effective size of hydrogen inclusion defects and takes this factor into account in the associated formulations. The analogy between this method and that of the invention relates to the distribution of inclusion cleanness defects being taken into account, but there is no other common point. In particular, the aim is in no way to determine any maximum inclusion in the specimen analyzed.

In the invention, the method starts with the observation that the distribution used is described statistically by a normal curve and that this curve is representative of the production through statistical control of the welding process, the defects involved in this case being blowholes and not inclusions.

By such analysis, the maximum blowhole size at +3 standard deviations in weld beads was 100 to 110 μm under the manufacturing conditions in question.

The benefit of the method lies in the fact that these blowholes are not detectable by standard methods and that this approach makes it possible to take into account defects that are much smaller than those given by the detection threshold of the usual nondestructive methods. This approach therefore justifies longer lifetimes than those that take the detectability thresholds into account.

From the determination of this size, the availability of defect fatigue curves and the dispersion of the results by fatigue levels it is possible to determine the correction factor to be imposed on the minimum and average values of the design curves, without having to use a calculation incorporating the hardness of the material (which calculation has meaning only in the case of steels and in the case of crack propagation).

BRIEF DESCRIPTION OF THE DRAWINGS

The method of evaluating the fatigue behavior of a specified welding technique applied to an example will now be described in reference to the appended drawings in which.

DESCRIPTION OF THE PREFERRED EMBODIMENTS

The specimens are produced for example using the following method. A cavity 12 is machined in a metal plate 10 of parallelepipedal shape and this cavity is filled with the alloy in question so as to form a welded joint 16. For the tests, resurfacing with TA6V alloy was carried out on Ti17 alloy plates.

The resurfacing operation is carried out using the same welding technique as that used for repairing the intended industrial parts. The same equipment is employed with the same welding parameters. The invention generally applies to welding modes that are fully controlled and can be defined by significant parameters. For deposition of metal with heating by means of a laser beam, the parameters are in particular those that characterize the beam, namely type, wavelength, focal length, beam homogeneity, energy density, distance to the target, shielding of the molten pool, etc.

The benefit of controlling the process stems from the observation whereby, upon solidifying, the metal outgases and creates blowholes or other defects, the size and the distribution of which are reproducible. When a family of parameters is set, the defects lie within a range of known shapes and sizes. In the case of welding titanium alloys, the defects are spherical blowholes generally having sizes between 30 and 70 μm.

Figure 1:
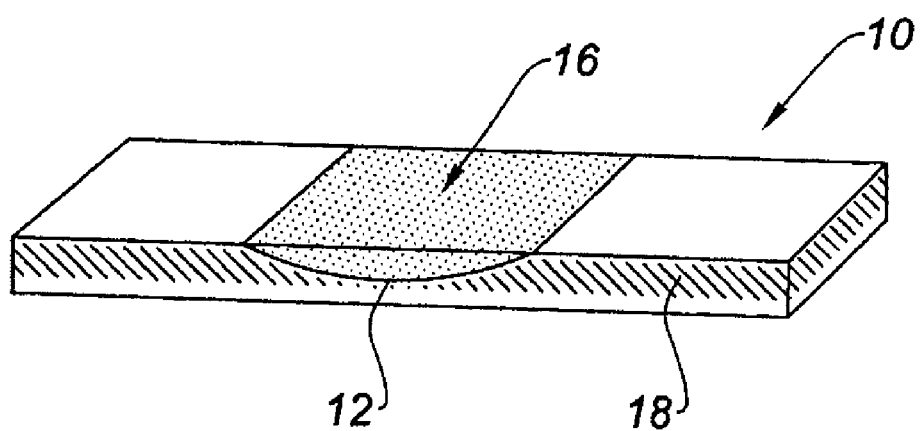
FIG. 1 shows a specimen produced using a welding technique, the reduction in fatigue behavior of which it is desired to determine.

The method of the invention therefore consists in carrying out cyclic fatigue tests on specimens. A specimen 18, corresponding to the hatched portion in FIG. 1, is thus cut from the metal plate 10 thus welded. The thickness of this specimen is less than the thickness of the welded joint 16 in its central portion. In this way, the middle region of the specimen consists only of the material that has been welded. A statistically sufficient number of specimens is produced. For titanium alloy specimens having around 5 to 6 relevant defects, with a size between 30 and 70 μm, this number is about 40. It corresponds, in the case of a normal law, to the sampling needed to obtain a value at more than 3 times the standard deviation for the required reliability (99.7%) in aeronautical design.

Figure 4:
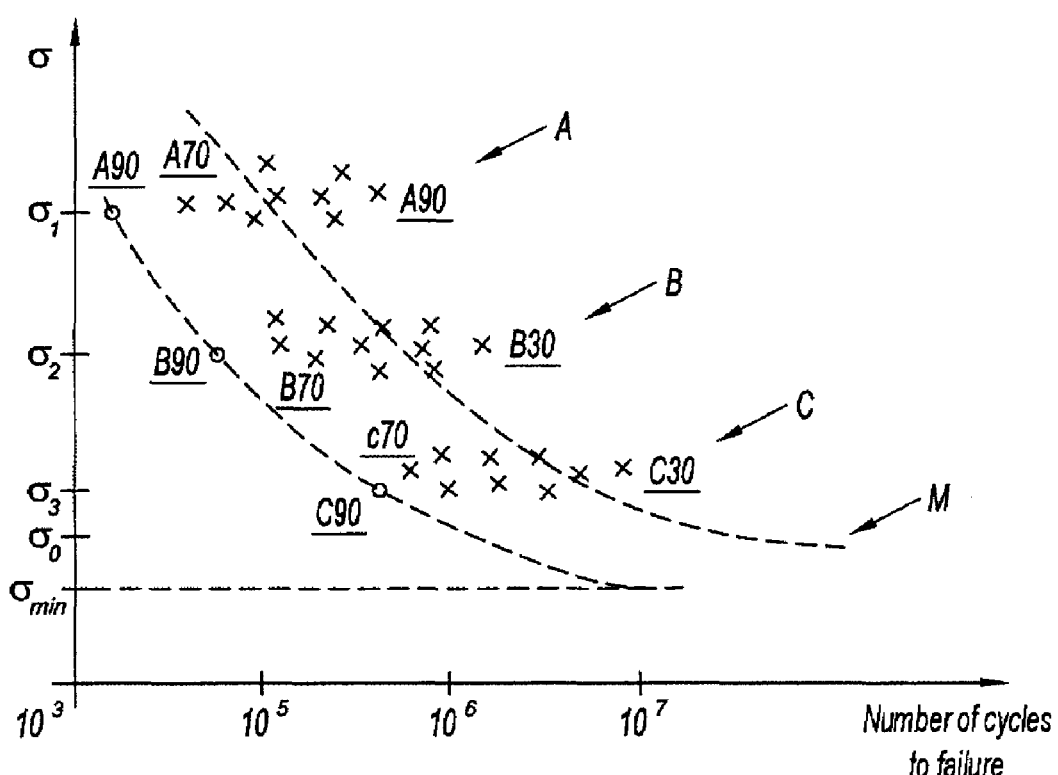
FIG. 4 is, for a given material, a plot of cyclic fatigue tests, in which each point corresponds to a test on a specimen with the number of cycles to failure plotted on the x-axis, on a logarithmic scale, and the applied alternating stress, in N/m$^2$, plotted on the y-axis.

The specimens are subjected to an axial vibration fatigue test. This test consists in placing the specimen between two jaws a certain distance apart and in exerting axial tensile forces on them, the intensity of which varies periodically, until failure. The alternating stress to which the specimen has been subjected and the number of cycles to failure are plotted for each specimen, in a diagram. The orthonormal reference frame is one in which the number of cycles is plotted on the x-axis, on a logarithmic scale, and the significant value of the alternating stress, such as the maximum value, is plotted on the y-axis. A distribution of points as shown in the plot in FIG. 4 is obtained. In this example, fatigue tests were carried out by applying three levels of alternating stress: $\sigma_1$, $\sigma_2$ and $\sigma_3$. Thus, three clusters of points, namely A, B and C, are obtained.

Figure 2:
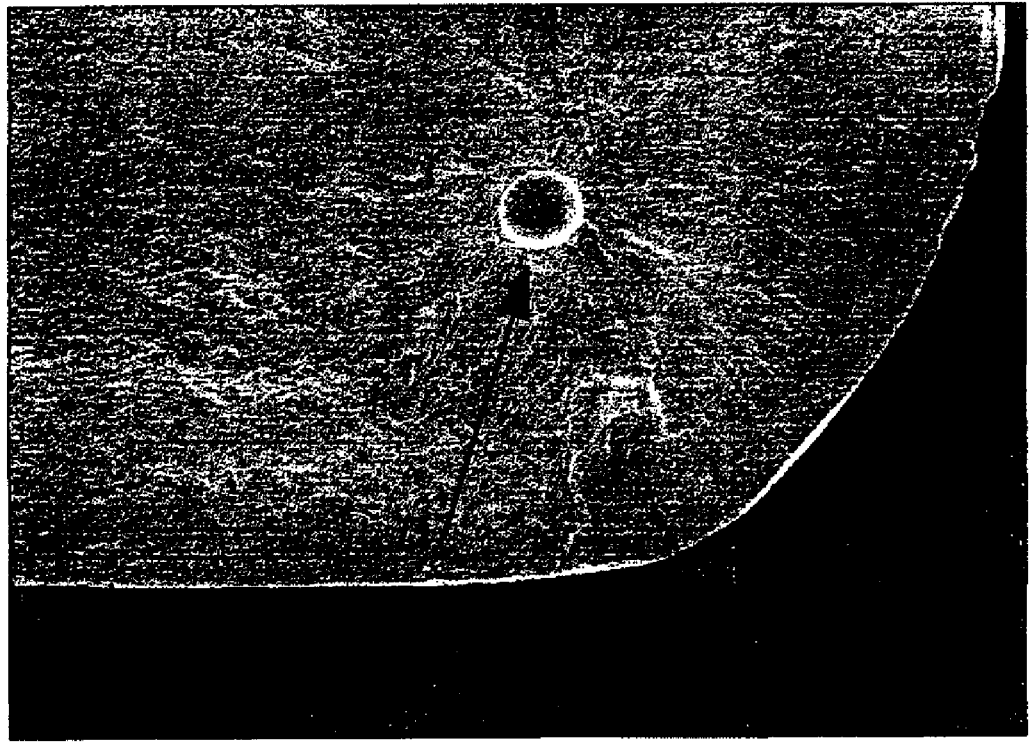
FIG. 2 is a fractograph of a specimen of FIG. 1.

A fractograph of each specimen is taken and the size of the relevant defect appearing in the fracture plane of the specimen is measured. The relevant defect is in fact that having originally the largest size in the specimen, since in fatigue the cracks appear firstly at such a defect. FIG. 2 shows a fractograph of a specimen manufactured using the above method with TA6V alloy resurfacing of a Ti17 alloy plate. The specimen failed after $9.5 \times 10^7$ cycles of cyclic tensioning under a maximum alternating stress of 350 MPa. The defect D has indeed a spherical shape and its diameter is estimated from the 200 μm scale on the edge of the photograph.

Figure 3:
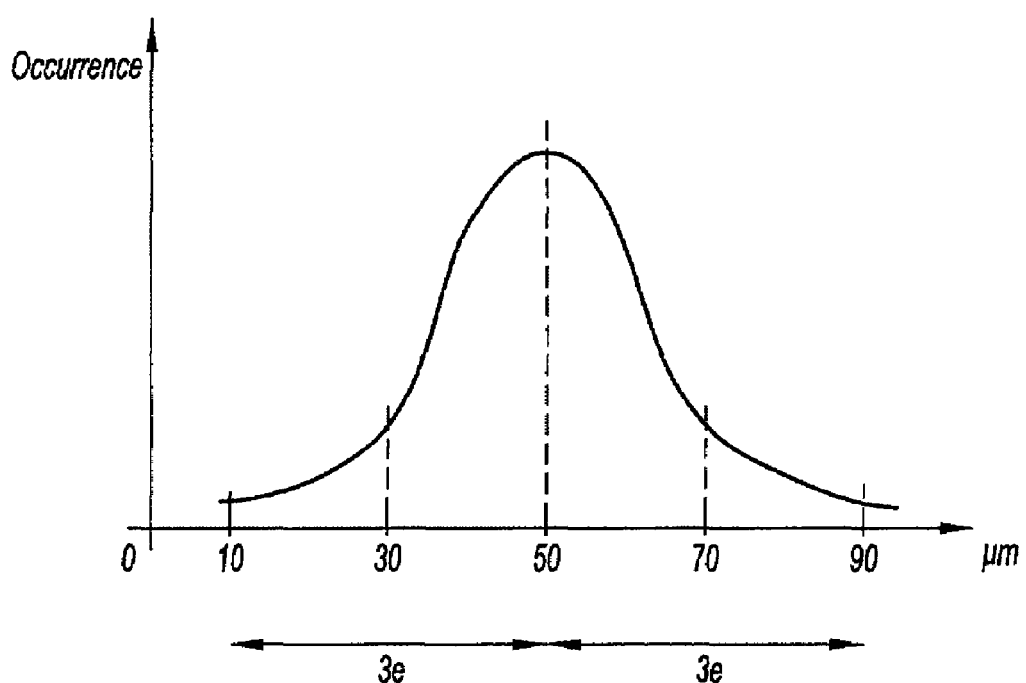
FIG. 3 is a diagram showing the distribution of defects as their frequency of occurrence.

A histogram of the number of defects having the same size is plotted. FIG. 3 shows a representation of such a histogram —it is verified that the distribution follows a normal Gauss law by applying conventional statistical tests (for example variance tests). Thus, the plot shown in FIG. 3 shows that all the defects for this series of specimens, produced under the same welding conditions, lie within the 30 μm to 70 μm range. The standard deviation of this distribution is calculated.

From this curve, the range of defect sizes extending between the mean size less three times the standard deviation and the mean size plus three times the standard deviation is determined by extrapolation. Within this + three times standard deviation to − three times the standard deviation (δ) range, statistically 99.7% of the occurrences occur, as is known.

Thus, here, the maximum blowhole size that is likely to be encountered with a probability of less than 0.3% is 90 μm.

Referring to FIG. 4, the minimum value σ1 of the cyclic stress that has resulted in fracture of a specimen within the batch subjected to the cyclic fatigue tests may be determined. This figure shows that, for each of the three clusters of points, the maximum recorded diameter, i.e. 70 μm, corresponds to the shortest lifetime in terms of number of cycles to failure, A70, B70 and C70 respectively. Likewise, the 30 μm defect diameter corresponds to the highest recorded lifetime, A30, B30 and C30 respectively. It may also be seen that these values allow the curve of the means, of the Wohler curve type, to be plotted. This curve M of the means makes it possible to determine the minimum stress $\sigma_0$ for a specified lifetime in terms of number of cycles.

For each of these clusters of points, the theoretical position of the point corresponding to a 90 μm defect diameter is determined from the histogram shown in FIG. 3, and the respective points A90, B90 and C90 are obtained. Next, a curve is plotted through these points, which is parallel to the curve of the means.

This curve thus makes it possible to determine the stress $\sigma_{min}$ for a specified lifetime.

From this point on the plot, the reduction relative to the curve of the means is readily found. This is either a reduction in lifetime or a reduction in maximum stress permitted in the part for a given number of cycles to failure.

A check is also made that the volume of material tested corresponds to the volume of the weld on industrial parts, especially repaired parts. This is because the quantity of defects encountered is linked to the volume of melted material. It is therefore important, on the specimens produced, for the material of all of the welded joints (volume of remelted material) to have a volume similar to that of the welded joints on the industrial parts. This volume lies preferably between 10% and 100% of the volume of the industrial welded joint. This volume is chosen so as to be "saturated" in terms of defects so as to be representative of the population of defects in the industrial joint. In practice, this saturation threshold is reached relatively rapidly because of the presence of very numerous defects for units of small volume (a few mm³).

The invention claimed is:

1. A method for evaluating the fatigue strength of welded joints produced by melting an alloy using a specified welding technique, which method comprises the following steps:
    a statistically significant number N of specimens are produced with a welded joint using said welding technique;
    each of the specimens is subjected to cyclic fatigue tests, with an alternating stress σ, until failure;
    the size of the relevant defect appearing in the fracture plane of the specimens is measured by fractography;
    a range of defect dimensions for which the probability of measuring by fractography a defect outside the range is less than a predetermined level of probability t is determined from the measured sizes; and
    the lowest stress $\sigma_{min}$ liable to cause the specimen to fail with a level of probability t is determined from this range.

2. The method as claimed in claim 1, wherein welded joints are produced on the specimens, the volume of which is between 10% and 100% of the welded joints on one of the parts to be assembled.

3. The method as claimed in claim 1, applied to evaluating the fatigue behavior of a titanium alloy assembly, the number of specimens of which is between 35 and 45, preferably 40.

4. The method as claimed in one of the preceding claims, the level of probability t of which is less than 1%.

5. The method as claimed in one of the preceding claims, the welding technique of which employs a laser beam to melt the alloy.

* * * * *